United States Patent
Yamada

(10) Patent No.: US 9,040,235 B2
(45) Date of Patent: May 26, 2015

(54) METHOD FOR SEQUENCING RNA BY IN-SOURCE DECAY USING MATRIX ASSISTED LASER DESORPTION IONIZATION TIME OF FLIGHT MASS SPECTROMETER

(75) Inventor: Masaki Yamada, Itabashi-ku (JP)

(73) Assignee: Shimadzu Corporation, Kyoto-Shi (JP)

( * ) Notice: Subject to any disclaimer, the term of this patent is extended or adjusted under 35 U.S.C. 154(b) by 741 days.

(21) Appl. No.: 13/215,029

(22) Filed: Aug. 22, 2011

(65) Prior Publication Data

US 2012/0080591 A1 Apr. 5, 2012

(30) Foreign Application Priority Data

Aug. 31, 2010 (JP) ................. 2010-193678

(51) Int. Cl.
*C12Q 1/68* (2006.01)
(52) U.S. Cl.
CPC .................... *C12Q 1/6872* (2013.01)
(58) Field of Classification Search
None
See application file for complete search history.

(56) References Cited

PUBLICATIONS

Hagan et al. Enhanced In-Source Fragmentation in MALDI-TOF-MS of Oligonucleotides Using 1,5-Diaminonaphthalene. J. Am. Soc. Mass. Spectrom. 23:773-777 (2012).*
Shimizu et al. Application of high-resolution EST and MALDI mass spectrometry to metabolite profiling of small interfering DNA duplex. J. Mass. Spectrom. 47:1015-1022 (2012).*

* cited by examiner

*Primary Examiner* — Samuel Woolwine
(74) *Attorney, Agent, or Firm* — Morgan, Lewis & Bockius LLP

(57) ABSTRACT

An analytic method is provided for obtaining much sequence information by causing in-source decay of modified RNA and non-modified RNA and generating many fragment ions. Particularly, a method for analysis wherein a matrix that efficiently causes decomposition by in-source decay of RNA of 20 bases or longer is used in an apparatus that has a laser of a wavelength commonly used in MALDI-TOF MS. A specimen containing RNA is subjected to matrix assisted laser desorption ionization time of flight mass spectrometry that uses 2,4-dihydroxyacetophenone as a matrix to obtain fragment ions derived from the RNA. The difference in mass between the peaks of ions in the fragment ions is used to analyze the sequence of the RNA.

4 Claims, 5 Drawing Sheets

ESTIMATED ISD MECHANISM OF RNA

OLIGONUCLEOTIDE FRAGMENT NAMING CONVENTION

SEQUENCE LISTING

```
<160> NUMBER OF SEQ ID NOS: 4

<210> SEQ ID NO 1
<211> LENGTH: 19
<212> TYPE: RNA
<213> ORGANISM: artificial
<220> FEATURE:
<223> OTHER INFORMATION: synthethic oligonucleotide
<220> FEATURE:
<221> NAME/KEY: modified_base
<222> LOCATION: (8)..(8)
<223> OTHER INFORMATION: 2'-O-methyadenosine at the 8th position

<400> SEQUENCE: 1
ucgaaguauu ccgcguacg                                             19
```

```
<210> SEQ ID NO 2
<211> LENGTH: 19
<212> TYPE: RNA
<213> ORGANISM: artificial
<220> FEATURE:
<223> OTHER INFORMATION: synthethic oligonucleotide

<400> SEQUENCE: 2
ucgaaguauu ccgcguacg                                                19

<210> SEQ ID NO 3
<211> LENGTH: 21
<212> TYPE: DNA
<213> ORGANISM: artificial
<220> FEATURE:
<223> OTHER INFORMATION: synthethic oligonucleotide
<220> FEATURE:
<221> NAME/KEY: modified_base
<222> LOCATION: (8)..(8)
<223> OTHER INFORMATION: 2'-O-methyladenosine at the 8th position
<220> FEATURE:
<221> NAME/KEY: misc_feature
<222> LOCATION: (1)..(19)
<223> OTHER INFORMATION: RNA

<400> SEQUENCE: 3
ucgaaguauu ccgcguacgt t                                             21

<210> SEQ ID NO 4
<211> LENGTH: 21
<212> TYPE: DNA
<213> ORGANISM: artificial
<220> FEATURE:
<223> OTHER INFORMATION: synthethic oligonucleotide
<220> FEATURE:
<221> NAME/KEY: misc_feature
<222> LOCATION: (1)..(19)
<223> OTHER INFORMATION: RNA

<400> SEQUENCE: 4
ucgaaguauu ccgcguacgt t                                             21
```

METHOD FOR SEQUENCING RNA BY IN-SOURCE DECAY USING MATRIX ASSISTED LASER DESORPTION IONIZATION TIME OF FLIGHT MASS SPECTROMETER

TECHNICAL FIELD

The present invention relates to an art for performing RNA sequencing by MALDI-TOF MS. This art is expected to be used in life sciences such as by pharmaceutical companies performing development work on nucleic acid drugs and companies engaged in the business of synthesis and sale of oligonucleotides.

BACKGROUND ART

With increased development activities in recent years in nucleic acid pharmaceutical, there is a need for a technology for the analysis of oligonucleotide sequences of about several dozen bases long. With nucleic acid drugs, a general practice is to increase in vivo retention by the introduction of an artificial moiety such as phosphorothioate esters and modified ribose 2'-OH groups. There is a need for a technology that can sequence nucleic acids that include an artificial moiety.

Examples of the use of MALDI-TOF MS to sequence oligonucleotides include a method (see Non-Patent Literature 1) wherein a ladder structure mass spectrum is obtained for RNA whose phosphodiesters have been partially hydrolyzed with an acid and the sequence is analyzed based on the mass difference between peaks, and a method (see Non-Patent Literature 2) wherein a RNA is sequentially decomposed with an endonuclease starting from either the 3'-end or the 5'-end, mass spectra are obtained over time and sequence information is obtained.

In-source decay (ISD) and MALDI-TOF MS are primarily used for the analysis of amino acid sequence of peptides (see Non-Patent Literature 3 and 4). However, there are several reported cases of their use for the analysis of nucleic acid base sequence (see Non-Patent Literature 5 and 6).

With respect to DNA that is 11 bases long, Non-Patent Literature 5 discloses the generation of fragment ions by irradiation with laser of a wavelength of 266 nm while using picolinic acid as a matrix.

With respect to DNA that is 7 bases long, Non-Patent Literature 6 discloses the generation of fragment ions using 2,5-dihydroxybenzoic acid (2,5-DI-113) as a matrix. Even though the literature does not identify the laser wavelength, based on the use of Voyager Elite (manufactured by Perspective Biosystems), the wavelength is estimated to be 337 nm.

Non-Patent Literature 7 discloses the analysis of a DNA sequence by in-source decay using a mixture of dihydroxyacetophenone (DHAP) and 1,5-diaminonaphtalene (DAN) as a matrix. The literature states that almost no fragments were detected when in-source decay was used on RNA.

Non-Patent Literature 8 discloses the use of 2,4-dihydroxyacetophenonematrix for the separation of 100-base long DNA and 102-base long DNA consisting of TC repeat sequences on a mass spectrum and their detection.

With base sequence analysis of nucleic acids using mass spectrometry, reflecting the cleavage site of the phosphodiester bonds, fragment ions that are generated from the nucleic acid are named as a, b, c, or d if they possess a 5'-OH group and as w, x, y or z if they possess a 3'-OH group (see Non-Patent Literature 9).

However, there are no reports of the analysis of sequences of RNAs (unmodified) and RNAs having modified groups based on the mass spectrum of fragment ions that are generated by in-source decay.

PRIOR ART LITERATURE

Non-Patent Literature

Non-Patent Literature 1: Bahr U. et al., Anal. Chem., 2009, 81, 3173-3179.

Non-Patent Literature 2: Gao H. et al., Rapid Commun. Mass Spectrom., 2009, 23, 3423-3430.

Non-Patent Literature 3: Takayama M. et al., J. Mass Spectrom. Soc. Jpn., 2002, 50, 304-310.

Non-Patent Literature 4: Demeure K. et al., Anal. Chem., 2007, 79, 8679-8685.

Non-Patent Literature 5: Juhasz P. et al., Anal. Chem., 1996, 68, 941-946.

Non-Patent Literature 6: Koomen J. M., et al., J. Mass Spectrom., 2000, 35, 1025-1034.

Non-Patent Literature 7: Shimadzu Application News, No. B17, 2009 年 10 月

Non-Patent Literature 8: Y. Yoshikawa, K. Nakajima, N. Kimura, M. Gonda, K. Okamoto, G. Tamiya, H. Inoko, "An efficient application of MALDI-TOF/MS coupled with microarray for detection of microsatellite polymorphisms.", Program Nr: 1239 from 2002 ASHG Annual Meeting, (online), (search performed on Aug. 18, 2010), Internet <URL: http://www.ashg.org/geneties/abstracts/abs02/f1239.htm>

Non-Patent Literature 9: McLuckey, S. A. et al., J. Am. Soc. Mass Spectrom., 1992, 3, 60-70.

OVERVIEW OF THE INVENTION

Problems to Be Solved by the Invention

With the method disclosed in Non-Patent Literature 1, the acid hydrolysis of phosphodiesters of RNA requires a 2'-OH group in the ribose. This means that phosphodiesters do not decompose in RNA whose 2'-OH group is modified for example by methylation. A problem with this method is therefore that the position of the base that is modified by methylation cannot be identified.

A problem with the method described in Non-Patent Literature 2 is that it is time-consuming and labor-intensive since various conditions such as enzymatic digestion time must be considered and mass spectrometry has to be performed over time.

A problem with the method described in Non-Patent Literature 5 is that the wavelength (266 nm) of the laser that is used for the in-source decay analysis of oligonucleotides is uncommon, thus limiting the apparatus that can be used for the analysis to only those apparatuses having a laser of the aforesaid wavelength.

Furthermore, with the method according to Non-Patent Literature 5, there is a description of an example of the analysis of a DNA fragment that is 11 bases long, but there is no description of the analysis using in-source decay of RNA of 20 bases or longer which are the objects of studies in the context of nucleic acid pharmaceutical.

The DNA that is analyzed in Non-Patent Literature 6 is seven bases long and the fragment ions that are obtained by in-source decay are few in number, thus providing only a partial sequence information and creating a problem that the sequence of RNA of 20 bases or longer which are being studied in the context of nucleic acid pharmaceutical cannot be analyzed.

As the literature states, a problem with the method according to Non-Patent Literature 7 is that the sequence of RNA cannot be analyzed by the in-source decay.

With Non-Patent Literature 8, what are being detected are solely the parent ions of a long-chain DNA. Fragment ions that allow sequencing are not detected.

The decomposition mechanism of peptides by in-source decay is believed to be triggered by the addition of a hydrogen atom to a carbonyl group. The cleavage of oligonucleotides by in-source decay is believed to be caused by the addition of hydrogen atom to a phosphodiester bond. This decomposition is expected to occur regardless of whether 2'-OH is present.

Non-Patent Literature 5 discloses that, according to the in-source decay fragment efficiency of oligonucleotides, the ion strength that can be obtained will be only several % of intact ions. Hence, to obtain in-source decay ions in abundance, a matrix is required whose ionization efficiency of the oligonucleotide is high.

In light of the above, it is the object of the present invention to provide an analytical method that can provide much sequence information by causing in-source decay of non-modified RNA and modified RNA and generating many fragment ions.

It is also the object of the present invention to provide an analytical method that uses a matrix that can efficiently cause decomposition by in-source decay of RNA whose length is 20 bases or longer using an apparatus having a laser of a wavelength commonly used with MALDI-TOF MS.

Solution

After diligent work, the present inventor discovered that 2,4-dihydroxyacetophenone efficiently causes in-source decay of RNA. The present inventor also discovered that commonly used nitrogen laser with a wavelength of 337 nm generated fragment ions by in-source decay when used with 2,4-dihydroxyacetophenone. The present inventor also discovered that 2,4-dihydroxyacetophenone causes in-source decay of RNA that includes modifications.

The present inventor completed the present invention based on the above knowledge.

The present invention includes the following inventions.

(1) A method for sequencing of RNA wherein a specimen including RNA is subjected to matrix assisted laser desorption ionization time of flight mass spectrometry that uses 2,4-dihydroxyacetophenone as a matrix to obtain fragment ions derived from the RNA by in-source decay and the sequence of the RNA is analyzed by the difference in mass between peaks of the fragment ions.

In the above, the RNA includes both non-modified RNA sand modified RNAs.

(2) The method for sequencing RNA described in (1) wherein the RNA has ribose with a 2' modified group.

(3) The method for sequencing RNA described in (2) wherein the RNA has a ribose with a 2'—O-methyl group.

(4) The method for sequencing RNA described in any one of either (1) through (3) wherein the RNA has a base length of 20 to 30.

Effects of the Invention

The present invention provides an analytic method wherein in-source decay of non-modified RNA and modified RNA is used to generate many fragment ions and thus to obtain much sequence information.

The present invention provides an analytic method wherein an apparatus having a laser of a commonly used wavelength with MALDI-TOF MS is used with a matrix that efficiently causes decomposition by in-source decay of RNA.

With the present invention, at least 90%—for example—of ions of an entire sequence can be assigned by the assignment of fragment ions that are characteristic of w-series, y-series and d-series fragment ions that are generated by in-source decay of the RNA being analyzed.

The present invention provides an analytic method that is useful in analyzing the sequence of RNA of 20 mers or longer which is the subject of nucleic acid pharmaceutical. The present invention also provides a simple means for the analysis of oligonucleotide sequences that does not require a pre-process such as an acid treatment.

EMBODIMENTS

1. RNA

Figure 1:
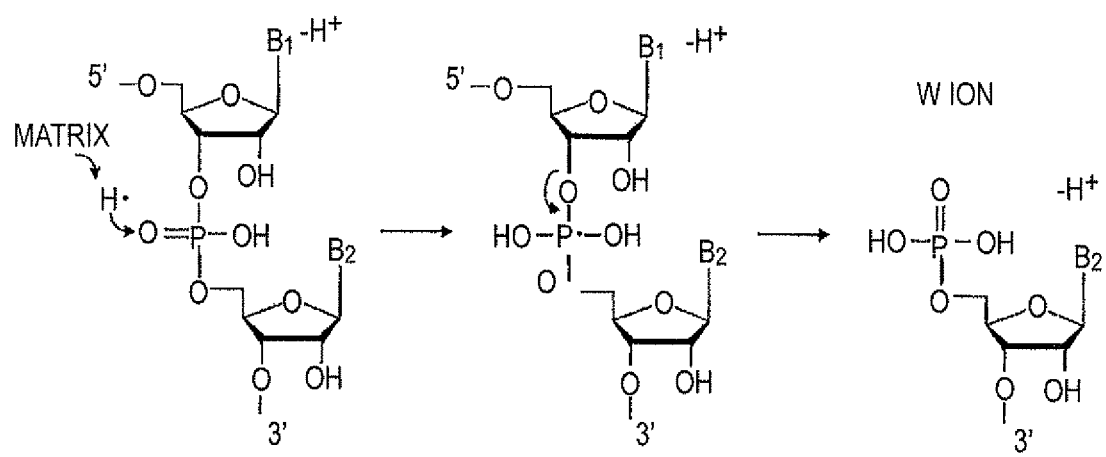
FIG. 1 shows the estimated mechanism by which RNA decomposes into a w-series by in-source decay. In the equation, $B_1$ and $B_2$ represent bases.

No particular limitations are imposed on the RNA (ribonucleic acid) that is covered by the present invention as long as the RNA has a base moiety of adenine (A), guanine (G), cytosine (C) and uracil (U), a sugar moiety of a ribose and a phosphate moiety of phosphate bonds. Also, with the present invention, the RNA includes both natural RNA and artificial RNA analogs. (In the specification, the term "non-modified RNA" may be used to refer to a type of natural RNA and the term "modified RNA" may be used to refer to a type of an artificial RNA analog.)

No particular limitations are imposed on the type of an artificial RNA analog. It may be a RNA whose base moiety is modified, whose sugar moiety is modified or whose phosphate moiety is modified. However, it is preferable for the modification to be acceptable in the field of nucleic acid pharmaceutical.

An example of a RNA whose base moiety that is modified is methylated cytosine.

Examples of RNA whose sugar moiety is modified are an RNA whose ribose has a 2' modification group, and linked nucleic acid (LNA) whose 2' position is bonded to the 4' position. Preferable examples include RNA whose ribose has a 2'—O-methyl group (2'—O-methylated RNA) and RNA whose ribose has a 2'-F group (2'-fluorinated RNA).

An example of RNA whose phosphate moiety is modified is phosphorothioate RNA wherein an oxygen atom in a phosphodiester bond (P=O) is replaced by a sulfur atom.

No limitations are imposed on the base length of the RNA, but a small RNA is preferred. One possibility is length of up to 30 bases long (e.g., 20 to 30 bases long). If the RNA is for nucleic acid pharmaceutical, 20 to 25 bases long is preferable, and 21 to 23 bases long is more preferable. If the RNA is a medical metabolite or if it is not limited to just pharmaceutical, the length can be less than 20 bases long.

No limitations are imposed on the amount of RNA that is used in the present invention. In particular, because the present invention is useful in handling very small quantities of RNA, the quantity of the RNA may be in the picomole level, e.g., 5 to 20 picomoles.

2. Matrix

With the present invention, 2,4-dihydroxyacetophenone is used as the matrix.

Fragment ions can be generated with widely used laser of the wavelength of 337 nm by using 2,4-dihydroxyacetophenone, and decomposition by in-source decay is efficient. No limitations are imposed on the amount of 2,4-dihydroxyacetophenone that is used, and those skilled in the art can decide the amount of 2,4-dihydroxyacetophenone to use just like any other matrix. For example, the quantity may be 2,000 to 50.000-fold (on a molar basis) of the RNA that is analyzed.

2,4-dihydroxyacetophenone is dissolved in a suitable solution and used. No limitations are imposed on the composition of the solution, and those skilled in the art may select a solution as deemed fit. For example, 2,4-dihydroxyacetophenone may be used as an aqueous solution of an organic solvent such as acetonitrile or methanol. No limitations are imposed on the concentration of the organic solvent, but an example is 30% to 50% (by volume).

With the present invention, it is preferable to use 2,4-dihydroxyacetophenone as the only matrix and not to mix with some other matrix. In particular, 2,4-dihydroxyacetophenone is not used as a mixture with 1,5-diaminonaphtalene (DAN) which is known as a matrix that efficiently causes in-source decay.

Matrix additives may be used with the present invention. Ammonium salts of an organic acid or inorganic acid may be used as a matrix additive. Specific examples include ammonium citrate dibase (ACDB), ammonium acetate (AA), ammonium chloride (ACl), ammonium citrate tribase (ACTB), ammonium fluoride (AF) and ammonium tartarate (AT).

No limitations are imposed on the amount of additives that are used, and the amount can be suitably decided by those skilled in the art. An example would be one-fourth to an equal amount (on a molar basis) as 2,4-dihydroxyacetophenone which is used as the matrix.

3. Mass Spectrometry

The RNA is mixed with the matrix and subjected to mass spectrometry. With the mass spectrometry, matrix assisted laser desorption ionization time of flight (MALDI-TOF) mass spectrometer is used, and fragment ions derived from the RNA are obtained by in-source decay (ISD). With MALDI-TOF mass spectrometry that uses in-source decay, the RNA is irradiated with a laser to simultaneously fragment the RNA inside the ion source. Excited molecular ions, i.e., fragment ions that are generated by the fragmentation, are detected to obtain RNA sequence information. Because fragment ions generated by in-source decay are detected in both the positive and negative modes, no limitations are imposed on the detection mode with regards to polarity, but the negative mode which is generally used for the measurement of oligonucleotides is preferred.

FIG. 1 shows the estimated in-source decay mechanism of RNA. As FIG. 1 shows, it is believed that the decomposition of RNA by in-source decay is triggered by the addition of hydrogen to the oxygen atom (P=O) in phosphodiester bond.

Similarly, the decomposition of a phosphorothioate type RNA by in-source decay is believed to be triggered by the addition of a hydrogen atom to the sulfur atom (P=S).

This means that decomposition by in-source decay occurs regardless of whether the modification is to the base moiety, the sugar moiety (2' hydroxyl group) or the phosphate moiety of the RNA.

Figure 5:
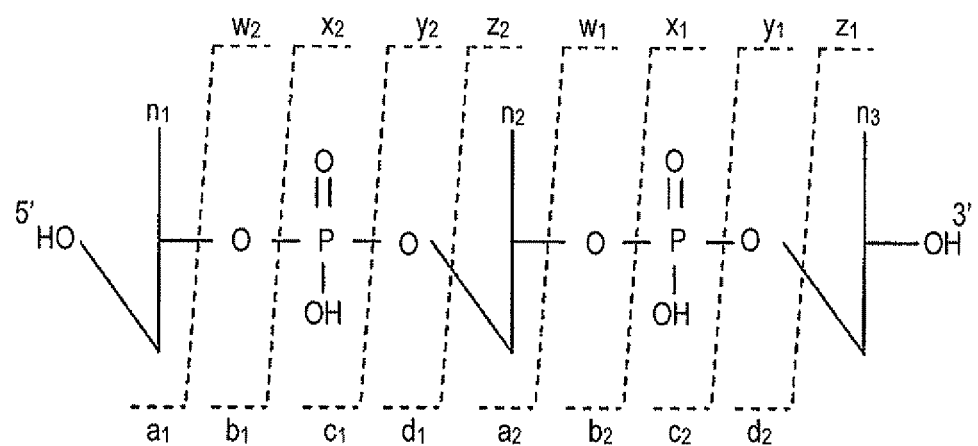
FIG. 5 shows the naming convention for RNA fragment ions. The structural equation of the RNA has been simplified for all parts except for the phosphate bond sites. $n_1$, $n_2$, and $n_3$ represent a nucleoside moiety.

With a method for RNA sequencing according to the present invention, by using the afore-described matrix, the in-source decay of RNA is efficiently performed, and fragment ions that are sufficient for providing the sequence information are obtained as w-series, y-series and d-series ions. Names are assigned to the respective fragment ions of the RNA based on the oligonucleotide naming convention shown in FIG. 5. The w-series fragment ions represent a series that are not generated by acid treatment and the like and are characteristic of in-source decay. The mass spectra that are obtained with an in-source decay represent the mass of the nucleotides that constitute the RNA as represented by the difference in mass between peaks of the ions in each series. Hence, by reading the difference in mass between the peaks, RNA can be very easily sequenced.

Embodiments

The present invention is further described next in detail with reference to its embodiments. It should be noted that the present invention is not limited to the embodiments described here. Unless specifically stated otherwise, all quantities represented in percent (%) are based on volume. The mass spectra that are shown for the embodiments plot the mass/charge ratio (m/z) along the horizontal axis and relative intensity along the vertical axis.

Embodiment 1

RNA samples were subjected to in-source decay analysis using as the matrix the following four compounds whose structure is shown below: 2,4-dihydroxyacetophenone; 2,5-dihydroxyacetophenone (for comparison); 2,6-dihydroxyacetophenone (tr comparison) and 2,4,6-trihydroxyacetophenone (for comparison). The RNA samples that were analyzed were 21 bases long with a 2'—O-methylated adenosine positioned as the eighth base from the 5 end. The specific sequence is 5 r-UCG AAG U(mA)U UCC GCG UAC GdTdT-3'. (SEQ ID NO: 3) (UCO AAG U(rnA)U UCC GCG UAC G is identified as SEQ ID NO: 1, and "mA" represents 2'—O-methyladenosine). This RNA sample is identified hereafter as 2'—O-methylated RNA.

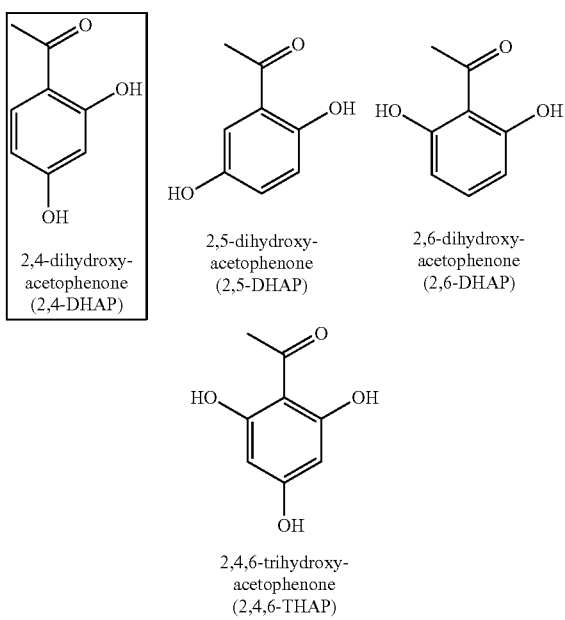

2,4-dihydroxy-acetophenone (2,4-DHAP)

2,5-dihydroxy-acetophenone (2,5-DHAP)

2,6-dihydroxy-acetophenone (2,6-DHAP)

2,4,6-trihydroxy-acetophenone (2,4,6-THAP)

Each matrix was dissolved in an aqueous solution that included 70 mM of ammonium citrate dibase and 50% acetonitrile. The 2,4-DHAP, 2,6-DHAP and 2,4,6-THAP were formulated to a concentration of 20 mg/ml in the aqueous solution while the 2,5-DHAP was formulated to a concentration of 10 mg/ml to prepare the matrix solution.

The 21-base long, 2'—O-methylated RNA with a concentration of 50 pmol/µl was mixed at a ratio of 1:1 (volume ratio) with a matrix solution. The mixed solution was applied to a stainless steel plate for MALDI-TOF MS measurement use, allowed to dry and subjected to MALDI-TOF MS measurement. AXIMA Confidence (registered trademark) manufactured by Shimadzu Corporation operating in the linear and negative mode was used for the MALDI-TOF MS measurement.

Figure 2:
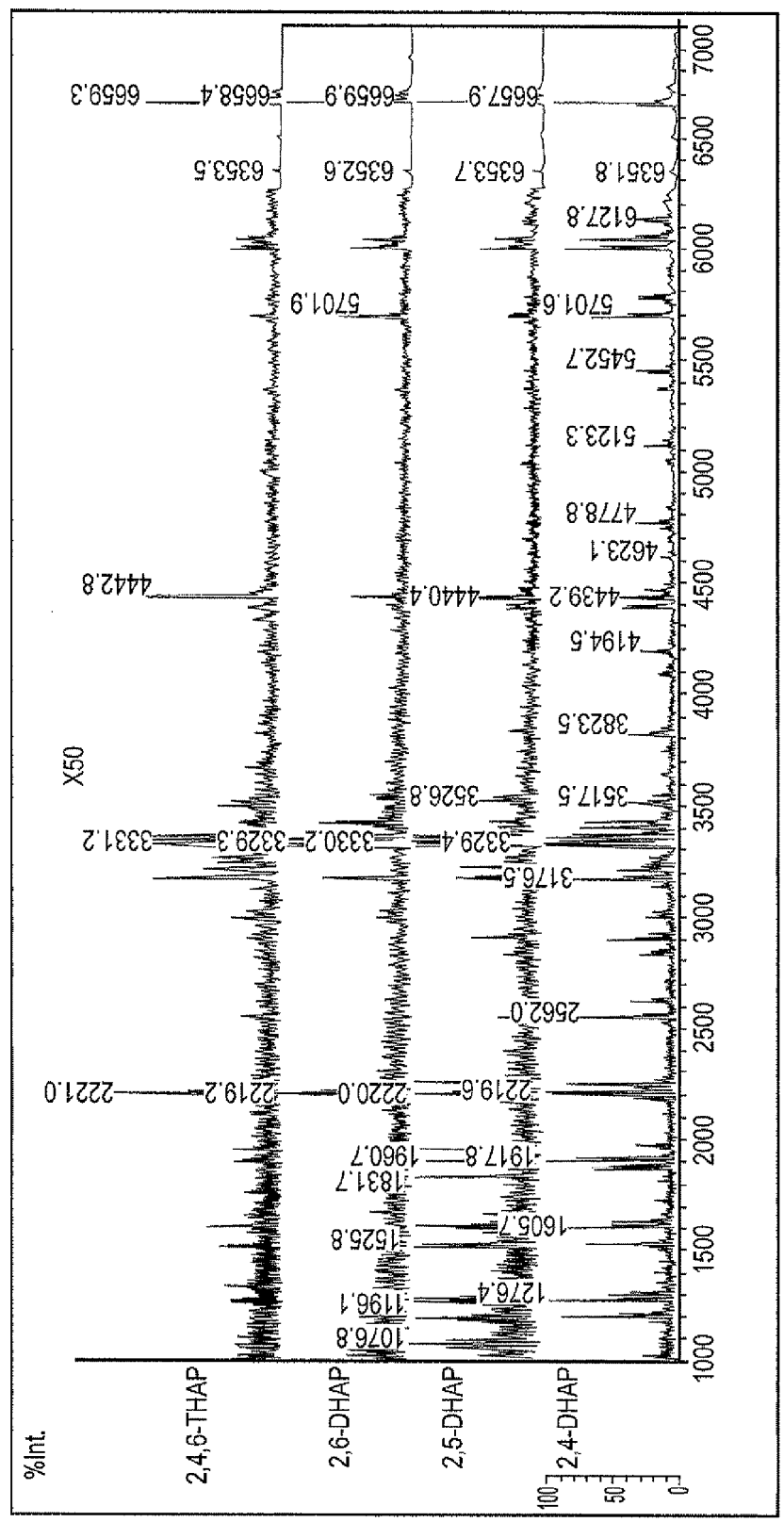
FIG. 2 shows a mass spectrum of fragment ions that were generated by in-source decay of RNA that is 21 bases long whose adenosine at the eighth base from the 5 end is 2'—O-methylated 5'-UCG AAG U(mA)U$^{LICC}$ GCG UAC GdTdT-3' where mA_represents 2'—O-methyladenosine: SEQ ID NO: 3. The spectra that are shown used: 2,4-DHAP ; 2,5-DHAP (for comparison); 2,6-DHAP (for comparison) and 2,46-THAP (for comparison) as the matrix.

FIG. 2 shows the mass spectrum that was obtained by the MALDI-TOF MS measurement. The ion intensity of the molecular related ion (m/z of 6658) of the RNA that was analyzed was the strongest when using 2,4-DHAP as the matrix as compared to the use of other matrices. Also as shown in FIG. 2, fragment ions in the vicinity of between m/z of 3500 and m/z of 6000 were detected with the strongest intensity as compared to the other matrices, indicating the high in-source decay efficiency.

Embodiment 2

Using 2,4-DHAP as the matrix, MALDI-TOF MS measurements were performed on 2'—O-methylated RNA and RNA that was not 2'—0-methylated (non-methylated RNA) in the same manner as with Embodiment 1. The specific sequence of the non-methylated RNA was 5'-UCG AAG UAU UCC GCG UAC GdTdT-3'. (SEQ ID NO: 4) (UCG AAG UAU UCC GCG UAC G is identified as SEQ ID NO:2).

Figure 3:
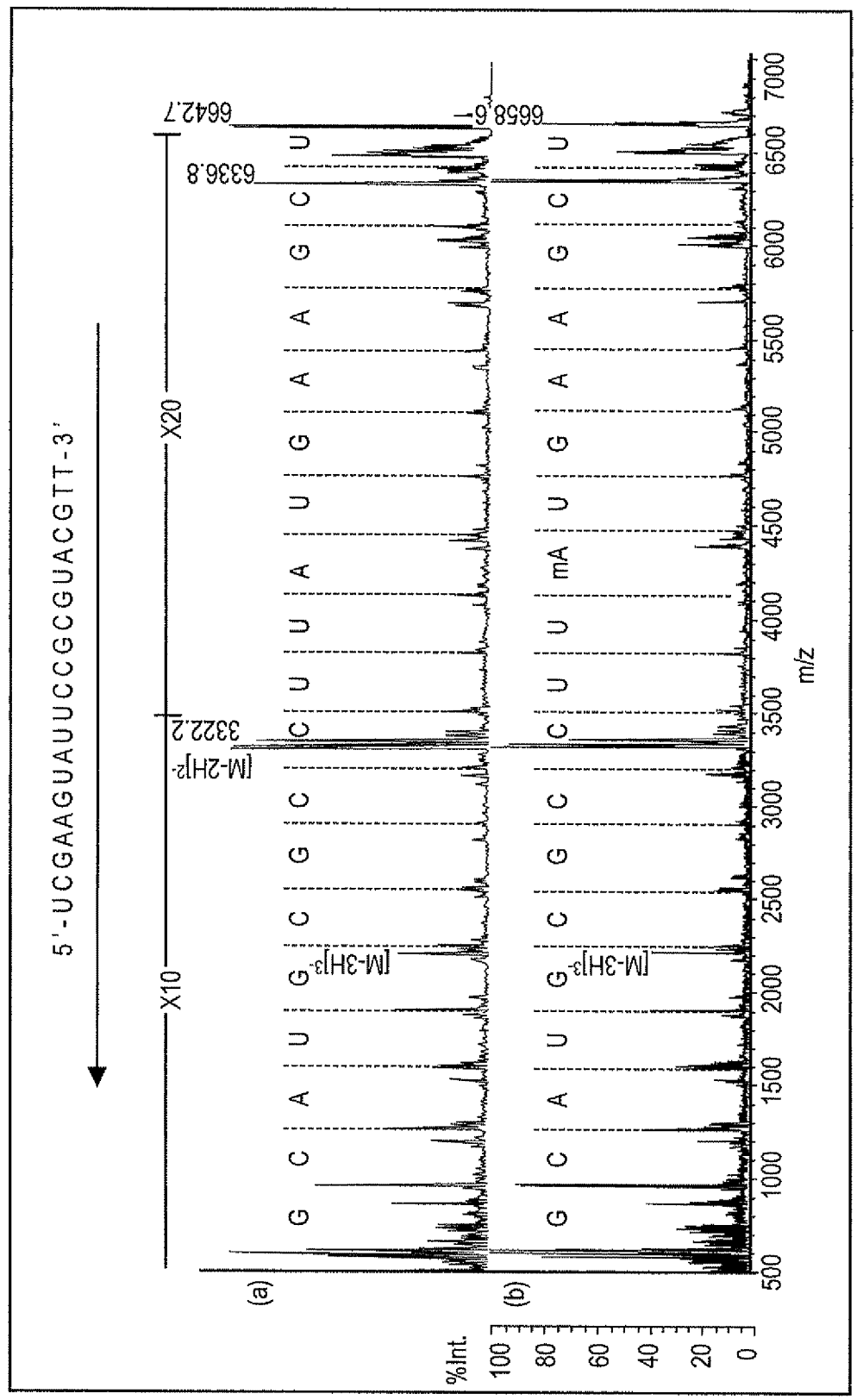
FIG. 3(a) shows the mass spectrum of fragment ions that were generated by the in-source decay of non-methylated RNA that is 21 bases long (SEQ ID NO: 4).
FIG. 3(b) shows the mass spectrum of fragment ions that were generated by in-source decay of RNA whose adenosine at the eighth base from the 5' end is 2'- O-methylated (SEQ ID NO:3.

FIG. 3 shows the mass spectrum of the fragment ions that were generated by in-source decay ((a): non-methylated RNA and (b): 2'—O-methylated RNA). w-series fragment ions are detected, and, among the 21 bases, all bases except for 2 bases at the 3' end could be associated with their ions, thus sequencing the RNA. The position of the methylation-modified base (mA) could also be confirmed.

COMPARISON EXAMPLE 1

2'—O-methylated RNA samples were prepared as 10 pmol/µl aqueous solution. A reagent solution was prepared containing 3-hydroxypicolinic acid (3-HPA) at a concentration of 50 mg/ml in an aqueous solution of 5% trifluoroacetic acid.

Figure 4:
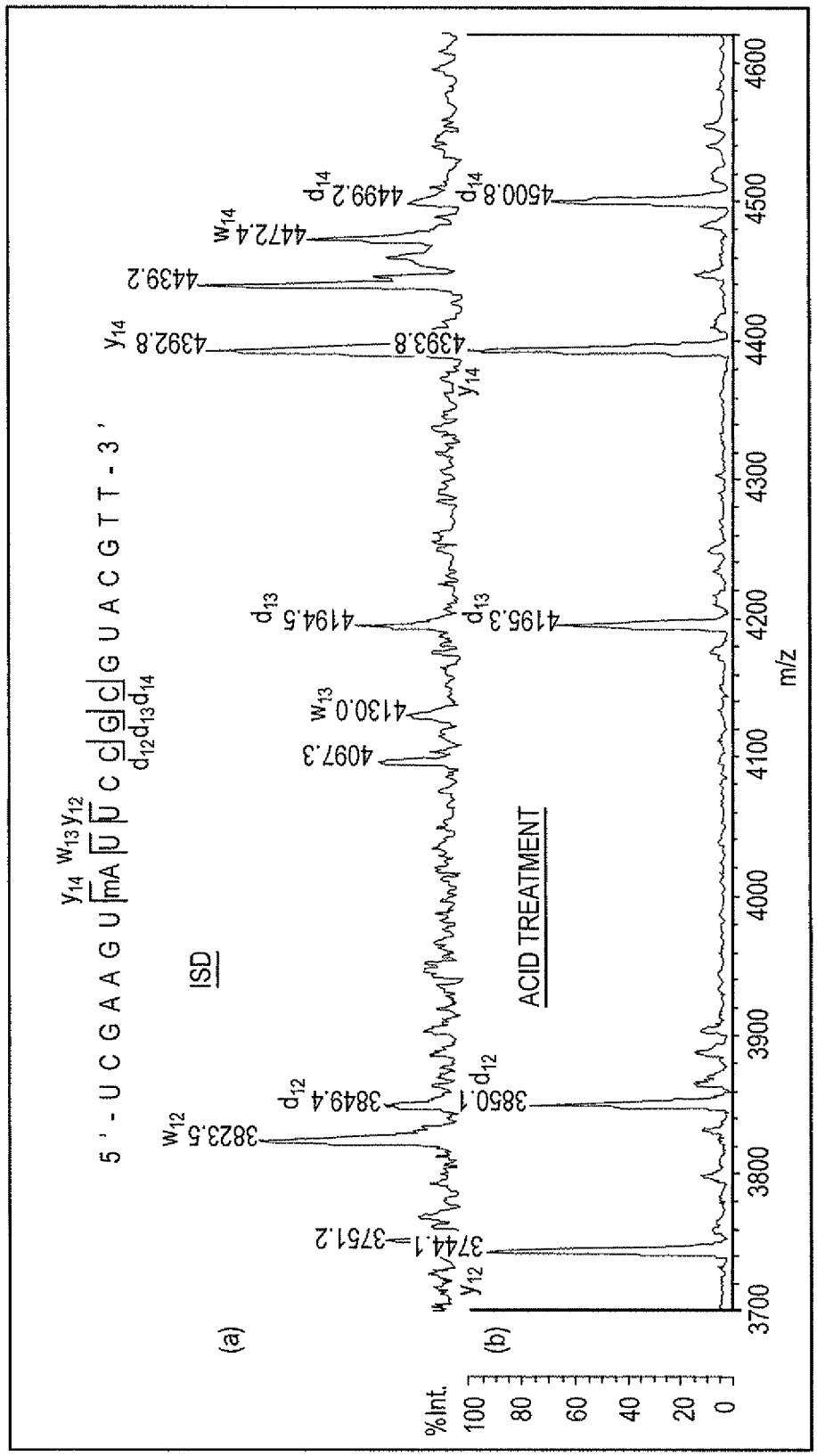
FIG. 4(a) shows the mass spectrum of fragment ions that were generated by the in-source decay of 2'—O-methylated RNA (SEQ ID NO: 3 ). For comparison.
FIG. 4(b) shows the mass spectrum of 2'—O-methylated RNA (SEQ ID NO: 3) that was pre-treated with an acid treatment.

The afore-described sample aqueous solution and the afore-described reagent solution were mixed in the same volume to prepare a reaction mixture solution (i.e., trifluoroacetic acid with a final concentration of 2.5%). 1 µl of the reaction mixture solution was immediately applied to a stainless steel plate for MALDI use and air-dried. 0.5 µl of 10 mg/ml ammonium citrate dibase aqueous solution was applied to the same dried spot and further air dried. After drying, measurements were taken using MALDI-TOF MS FIG. 4(b) shows the mass spectra obtained by MALDI-TOF MS measurement after an acid treatment. FIG. 4(a) shows an enlarged view of a portion (m/z between 3700 and 4600) of the mass spectra shown in FIG. 3(b) for a 2'—O-methylated RNA sample obtained as embodiment 2.

Because, as FIG. 4(b) shows, y13 was not detected after the acid treatment, it was confirmed that methylation site was not severed. On the other hand, as FIG. 4(a) shows, since the w13 ion was detected in the fragment ions generated by in-source decay, it was confirmed that the phosphodiester bond was broken regardless of methylation or not.

Sequence Listing Free Text

SEQ ID NO: 1 is a synthetic oligonucleotic whose eighth position is 2'—O-methyladenosine.

SEQ ID NO: 2 is a synthetic oligonucleotide.

SEO ID NO: 3 is a synthetic oligonucleotide of SEQ ID NO: 1 with dTdT appended at the 3'end.

SEQ ID NO: 4 is a synthetic oligonucleotide of SEQ ID NO: 2 with dTdT appended at the 3' end.

What is claimed is:

1. A method for sequencing RNA, comprising:
subjecting a specimen containing RNA to matrix assisted laser desorption ionization time of flight mass spectroscopy using 2,4-dihydroxyacetophenone as a matrix to obtain fragment ions derived from said RNA by in-source decay; and
analyzing said RNA sequence by the difference in mass between peaks of said fragment ions.

2. The method for RNA sequencing according to claim 1 wherein said RNA has a 2' modified group in the ribose.

3. The method for RNA sequencing according to claim 2 wherein said RNA has a 2'—O-methyl group in the ribose.

4. The method for RNA sequencing according to claim 1, wherein said RNA has a length of between 20 and 30 bases.

* * * * *